United States Patent [19]
Barnett et al.

[11] Patent Number: 5,911,500
[45] Date of Patent: Jun. 15, 1999

[54] LIGHT TUNNEL

[75] Inventors: Linda G. Barnett, Richmond; Robert T. Hinnen; Mark Overmyer, both of Kansas City, all of Mo.

[73] Assignee: Stuppy Incorporated, Kansas City, Mo.

[21] Appl. No.: 08/962,155

[22] Filed: Oct. 31, 1997

[51] Int. Cl.$^6$ .................................................. F21V 7/00
[52] U.S. Cl. ..................... 362/249; 362/253; 362/145; 362/346; 362/298
[58] Field of Search .............................. 362/33, 147, 145, 362/152, 253, 234, 297, 298, 301, 346, 367, 249

[56] References Cited

U.S. PATENT DOCUMENTS

| | | | |
|---|---|---|---|
| 4,669,033 | 5/1987 | Lee | 362/346 |
| 4,733,337 | 3/1988 | Bieberstein | 362/202 |
| 4,998,189 | 3/1991 | Guggemos | 362/278 |
| 5,456,023 | 10/1995 | Farnan | 362/96 |

*Primary Examiner*—Thomas M. Sember
*Attorney, Agent, or Firm*—Hovey, Williams, Timmons & Collins

[57] ABSTRACT

A light tunnel (10), to be used for close inspection of items (24) therein, includes a framework (12) comprised of an outer structure (30) and inner assembly (34) which support sheets of material (64) to define a pair of opposed side walls (16) and (18) and an arched top wall (20). An inner surface (42) of said walls being highly reflective to direct the light rays emanating form a light source (46) from the walls to the item to be inspected.

9 Claims, 4 Drawing Sheets

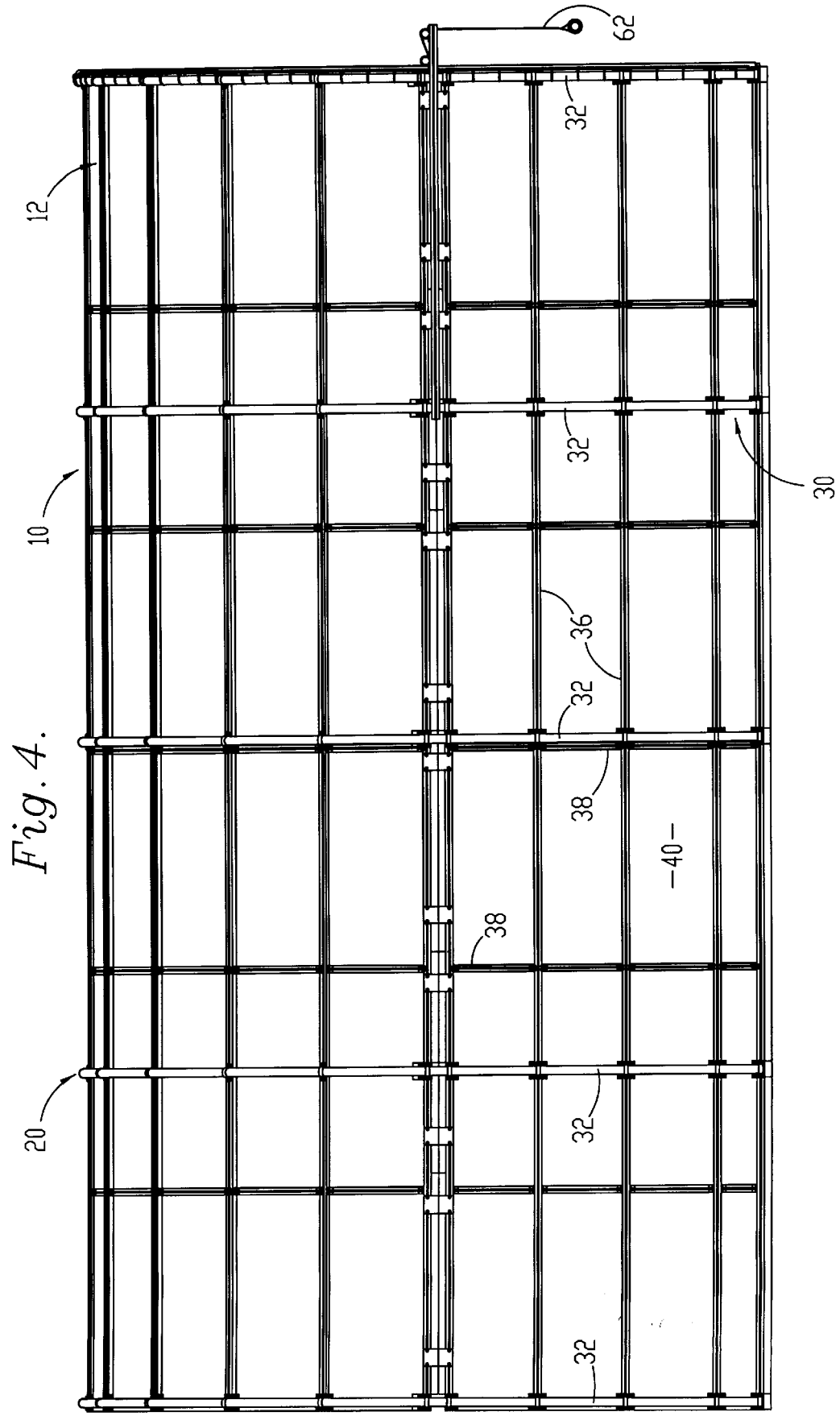

LIGHT TUNNEL

BACKGROUND OF THE INVENTION

1. Field of the Invention

This invention concerns a light tunnel which is particularly intended for use in inspecting items placed therein such as, for instance, a vehicle, to locate and determine flaws in the finish or sheet metal work of the vehicle so that these may be appropriately corrected. This inspection is permitted by providing a tunnel having a framework which carries reflective means in the interior thereof, there being a light source in the tunnel for directing light on the reflective means, which light in turn is reflected against the item within the tunnel, such as the vehicle.

2. Description of the Prior Art

Inspection of items such as vehicles just leaving the production line has usually been accomplished by manual visual or physical inspection, which is unsure and inaccurate in absolutely determining whether the paint finish or the sheet metal of a vehicle is flawed. It is of course important that this be determined before the vehicle is delivered to the ultimate purchaser.

Other means for inspecting the finish of a vehicle or, for that matter, other items which have a high finish would include portable light sources directed on the item or even sensing devices to be passed over the surface of the item.

It has not been known to create a light tunnel in which the entire item may be totally placed for a final inspection prior to delivery and which light tunnel includes a framework carrying sheet material presenting side walls and an arched top wall with reflective material being carried by said walls and presenting an uninterrupted inner surface which will reflect light back on to the item, the light emanating from a source spanning the length of the tunnel at essentially the juncture between the side walls and the top wall.

SUMMARY OF THE INVENTION

The present invention achieves the result of facilitating the rapid and thorough inspection of the exterior of an item by presenting an area, within the tunnel, which may totally receive the item to be inspected such as, for instance, a vehicle just leaving the assembly line.

To accomplish this result, the light tunnel is created from a framework having an outer structure and an inner assembly to support reflective material in the form of an acrylic, semi-rigid sheet material which has an outer and an inner surface, the inner surface being an uninterrupted reflective surface.

The sheet material is held in place by the inner assembly so as to present a pair of opposed side walls extending the length of the tunnel and an arched top wall extending upwardly from the spaced side walls to form the top of the tunnel.

A light source is positioned at the opposed junctures between each of the side walls and the top wall, the light source presenting two sources of light, the first source being directed toward the inner, reflective surface of the side wall and the second source being directed toward the inner, reflective surface of the top wall. These walls serve to return the reflected light to the item, which is positioned within the tunnel, the tunnel being of sufficient longitudinal and vertical dimensions to permit placement therein of an item to be inspected, such as a vehicle.

There are ingress and egress openings at opposed ends of the tunnel for permitting the movement of a vehicle into and out of the tunnel, with doors being positioned to effectively close said ingress and egress openings against the invasion of exterior light so that the light within the tunnel is all generated by the artificial light source positioned within the tunnel and extending substantially the full length thereof.

By placing a vehicle within the tunnel, a person may rapidly, conveniently and thoroughly inspect the finish thereof to see if there are any flaws in construction or "dings" which need to be dealt with prior to final delivery of the vehicle to the consumer. To this end, the light tunnel may be positioned at the end of the assembly line and the production conveyor could extend through the light tunnel so that it was the last stop on the assembly line producing the vehicle.

BRIEF DESCRIPTION OF THE DRAWINGS

FIG. 4 is a side elevational view of the light tunnel;

DESCRIPTION OF THE PREFERRED EMBODIMENT

Figure 1:
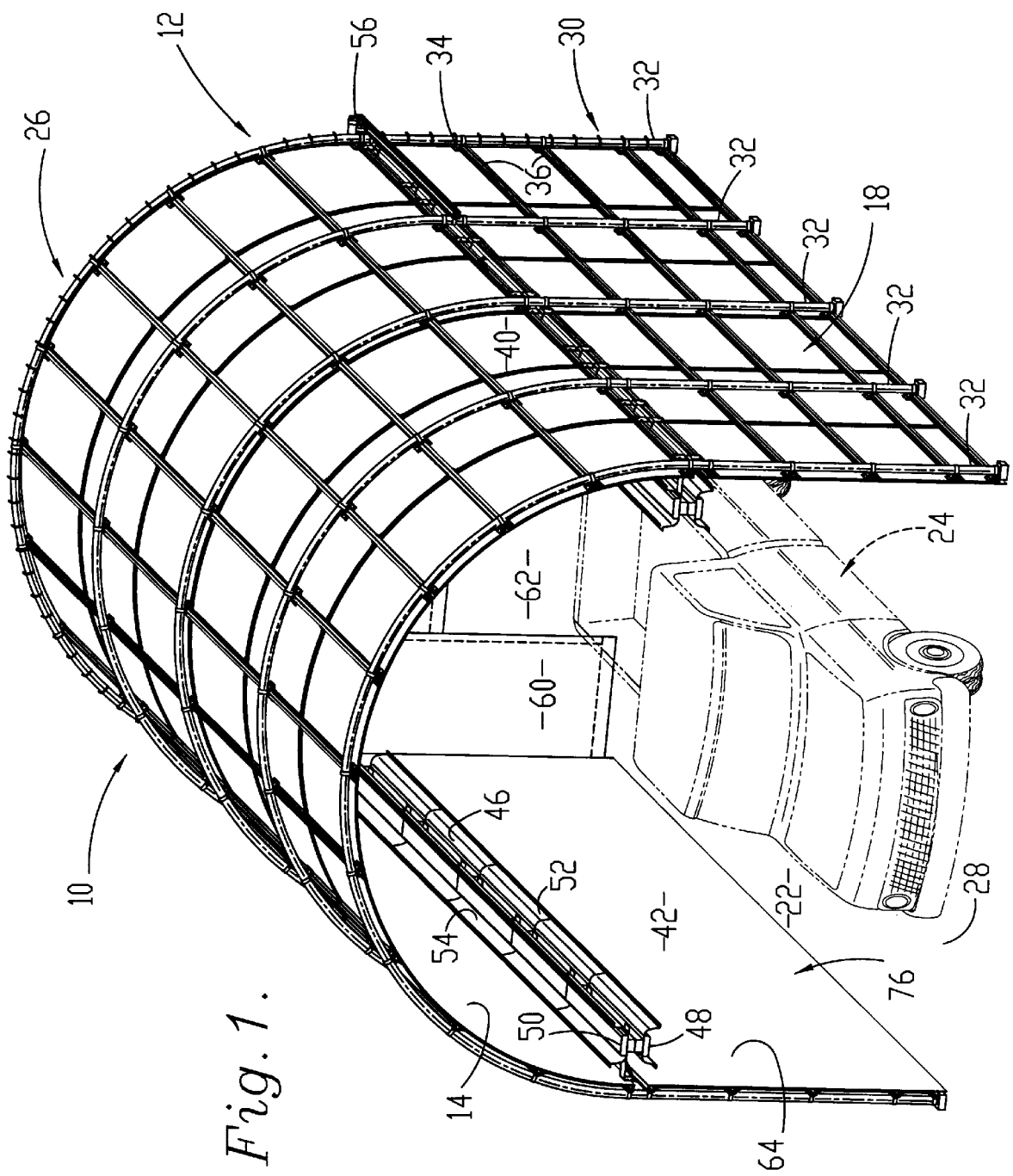
FIG. 1 is a perspective view of the light tunnel in use with a vehicle positioned therein.

The light tunnel 10 is best shown in FIG. 1 and has, as its major components, a framework 12 and reflective means 14 carried by the framework 12, the tunnel having a pair of opposed side walls 16 and 18 joined by an arched top wall 20, the framework 12 carrying the reflective means 14 in the configuration determined by that of the framework 12 which is preferably as illustrated in FIG. 1. The tunnel defines an area 22 within which the item to be inspected may be positioned, the item as illustrated in the drawings being in the form of a vehicle 24 which may be driven into the area 22 or moved there into by a production conveyor, through an ingress opening 26 and ultimately removed through an egress opening 28.

The framework 12 includes an outer structure 30, the outer structure 30 being, in the form of the invention as chosen for illustration, in the form of a plurality of arched members 32, five of such members being shown in the embodiment chosen for illustration. Members 32 are preferably of steel pipe whereby to give overall rigidity to the framework 12 and to serve in retaining the reflective material in the desired configuration.

Positioned within the outer structure 30 of the framework 12 is an inner assembly 34. The inner assembly includes a plurality of horizontally extending stringers 36 which extend the length of the light tunnel 10 and are suitably secured to the arched members 32 which constitute the outer structure 30 of the framework 12.

Positioned vertically between the horizontal stringers 36 are suitable braces 38 which are vertically disposed whereby to add rigidity to the inner assembly 34.

The reflective means 14 is in the form of sheets of a thermal plastic fire retardant semi-rigid material which is initially configured to conform to the interior configuration of the tunnel 10; that is, the side walls 16 and 18 are constituted of flat sheets of reflective material and the top wall 20 is constituted of a number of sheets of reflective material which are arcuate in configuration and which are suitably hoisted into place and attached to the stringers and braces of the top wall 20.

Figure 7:
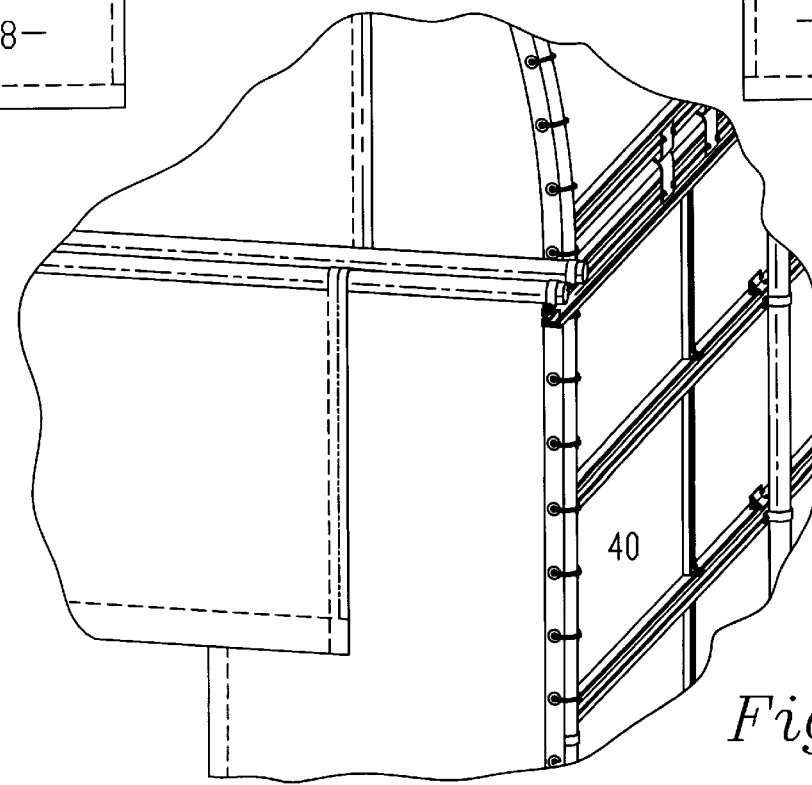
FIG. 7 is a fragmentary corner view of an upper corner at the rear end of the light tunnel as shown in FIG. 1.

The sheets of material which constitute the side walls and top wall have an outer surface 40 and an inner surface 42. The outer surface 40 is connected to the framework as best shown in FIG. 7 by means of suitable double faced tape or mechanical fasteners such as 44.

The inner surface 42 of the sheets of material is uninterrupted to prevent any distortion of the light which is directed onto such inner surface 42 and to present a clear, highly reflective surface, which may be suitably coated or textured to achieve maximum reflection of the light onto the item 24 to be inspected.

The light for the interior of the tunnel 10 is provided by a light source 46 which is in the form of fluorescent tubing extending substantially the full length of the tunnel 10 at the juncture between the respective side walls 16 and 18 and the bottom of the top wall 20. The light source includes a first source 48 and a second source 50, the first source being directed downwardly by a reflector 52 onto the inner surface 42 of the corresponding side wall 16 or 18 and thence, by reflection, onto the item 24.

Likewise, the second light source 50 is directed upwardly as by reflector 54 towards the inner surface of the top wall 20 and thence toward the item 24.

The light source 46 is supported in its horizontal position by a beam 56 which is positioned at the juncture between the side walls 16 and 18 and the bottom of the arched top wall 20.

Figure 2:
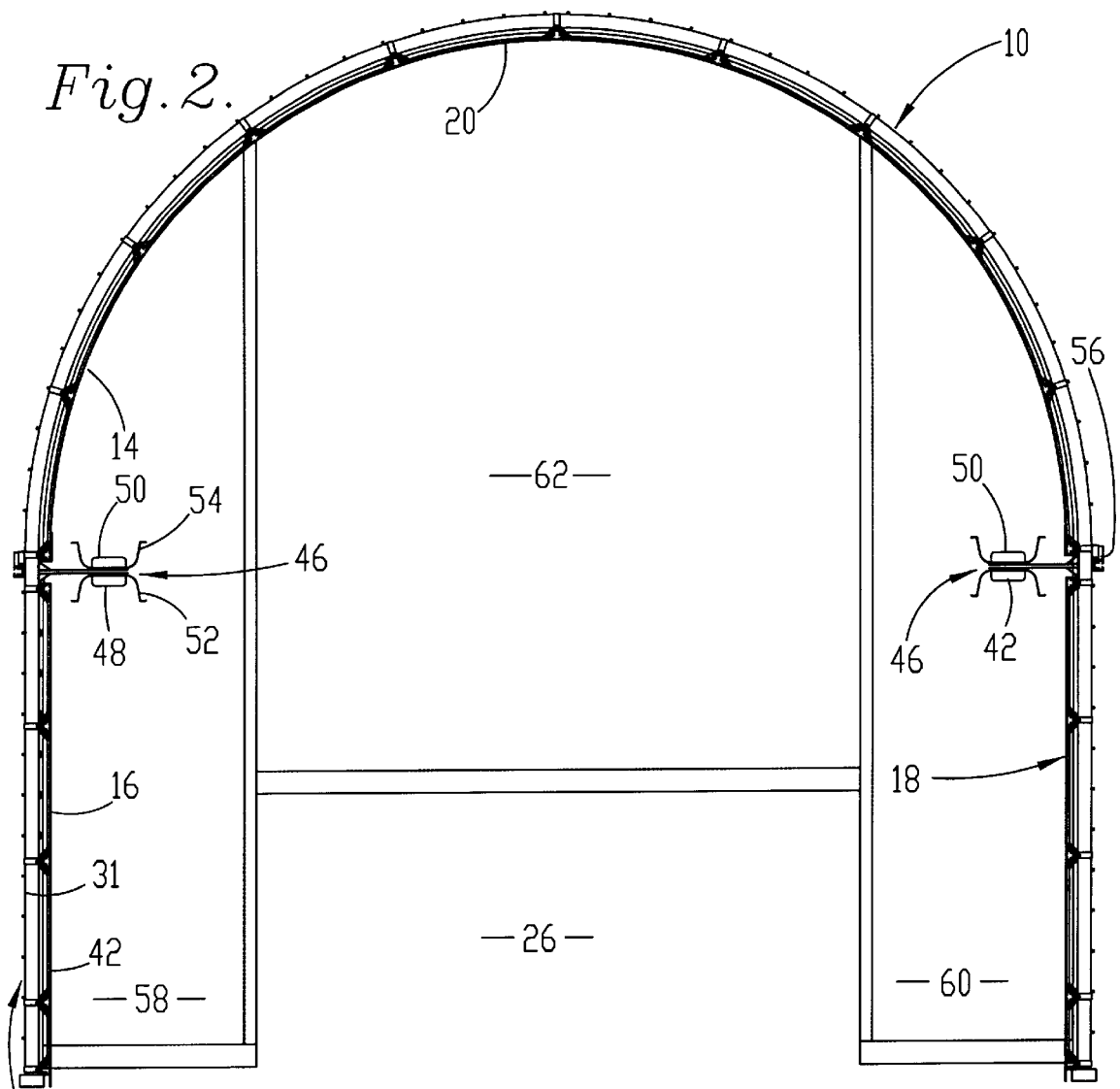
FIG. 2 is a front elevational view of the light tunnel as shown in FIG. 1.
Figure 5:
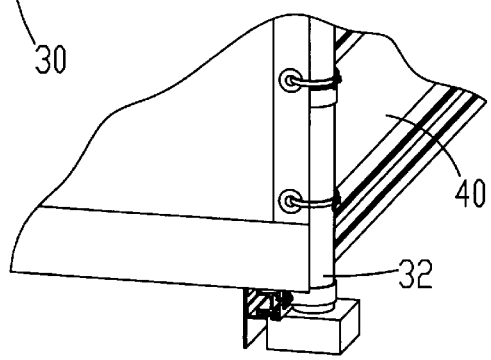
FIG. 5 is a fragmentary perspective view of a lower corner at the rear of the tunnel.
Figure 6:
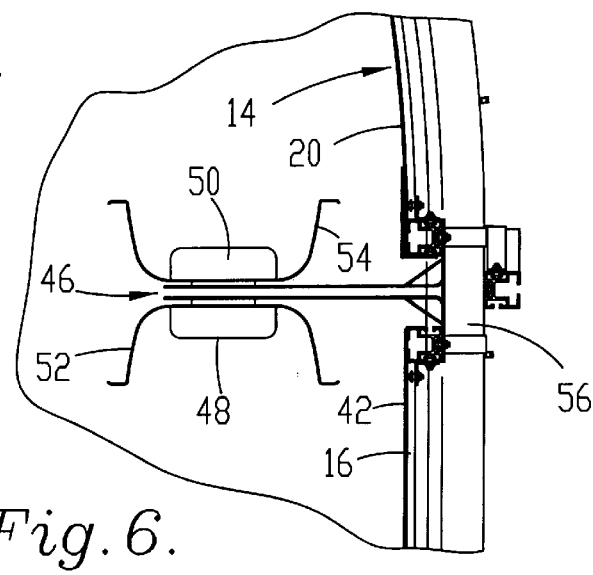
FIG. 6 is a fragmentary end elevational view of the framework and light source.
Figure 3:
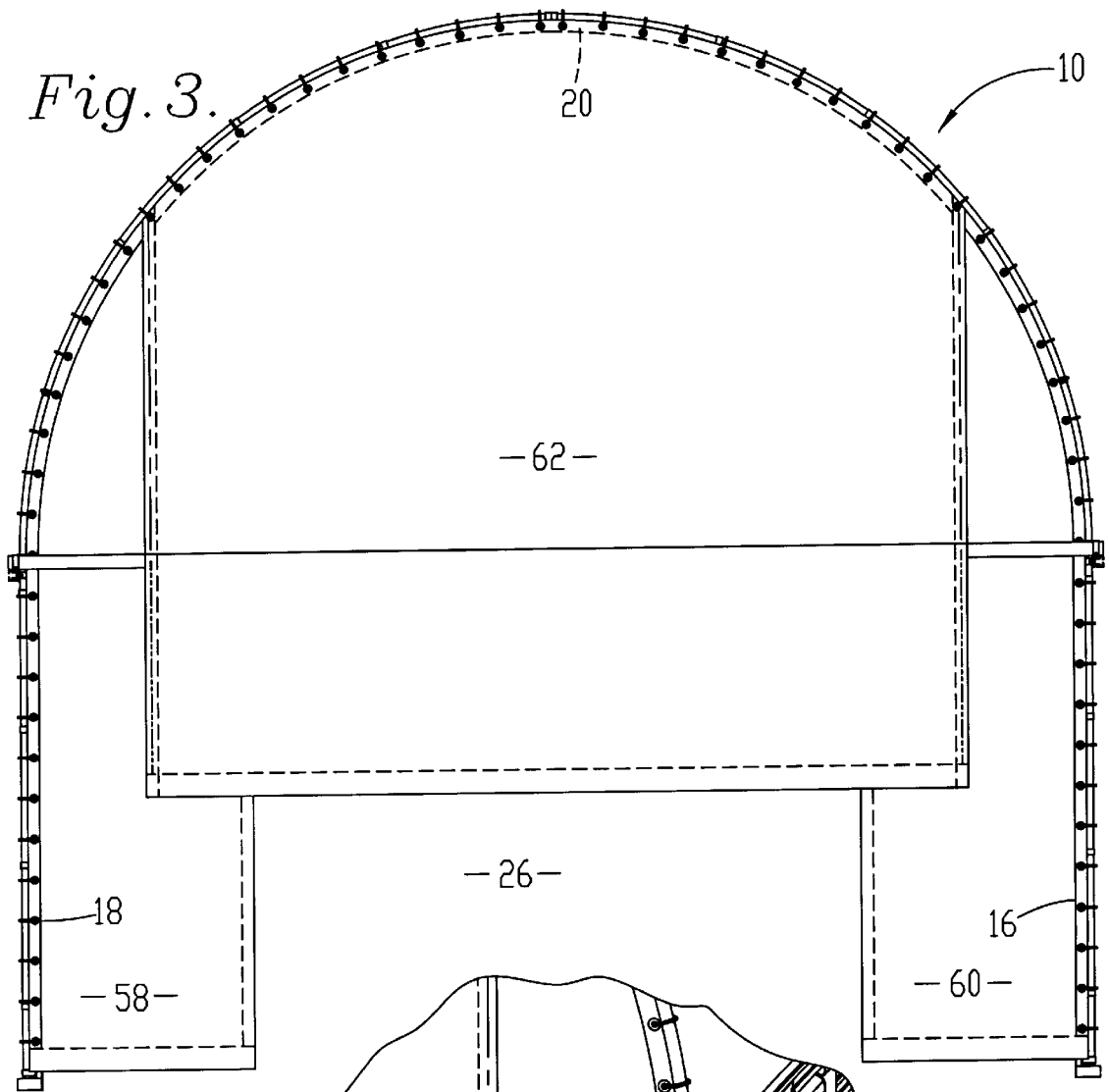
FIG. 3 is a rear elevational view of the light tunnel as shown in FIG. 1.

In order to position the item, such as a vehicle 24, within the tunnel 10, the ingress opening 26 may be utilized. However, when the tunnel is in operation; that is, the light source is on and an item is being inspected, it is desirable to minimize the exterior light which reaches the interior of the tunnel and thus the ingress opening 26 is bracketed by a pair of canvas curtains 58 and 60, as best illustrated in FIG. 2 and between which extends a flexible door panel 62.

The egress end 28 of the light tunnel is shown in FIG. 1 as being open, but it will be appreciated that suitable closure means may be utilized for the egress opening 28 as are described above with respect to the ingress opening 26. The use of the closure curtains 58 and 60 and the door panel 62 permits the area 22 to be confined against the intrusion of exterior light and permits the utilization of the specialized light source such as 46 to reflect upon the interior especially reflective surface 42 of the side walls and the top wall and thus direct maximum light upon the item to be inspected such as the vehicle 24 chosen for purposes of illustration.

It will be appreciated that the light tunnel 10 may be of any dimension and could be made larger to inspect, for instance, a larger vehicle or could be made smaller to receive for inspection an item of less dimensions such as, for instance, a consumer product like a washer or a dryer, where it is desired to have a high finish with no blemishes or flaws.

The light tunnel 10 may be readily erected in its desired position by forming the arched members 32 from piping, erecting the same; then attaching to the outer structure 30 defined by the arches 32 the inner assembly 34 in the form of stringers and braces as described and illustrated.

Once this framework has been created, the sheets of material are attached to the inner assembly with the reflective surface facing inwardly and the outer surface being utilized for attachment to the members of the inner assembly through suitable fastening means such as tape, screws, or other suitable fasteners. The sheets of material 64 which constitute the reflective means 14 may be formed from an acrylic/PVC thermoplastic sheet such as is sold by Kleerdex Company under the trademark KYDEX T, although equivalent materials would be acceptable. As will be appreciated, a highly reflective inner surface 42 is particularly desirable, while the outer surface may be utilized for connecting to the framework 12.

We claim:

1. A light tunnel used for close inspection of items therein comprising:

a framework;

reflective means carried by the framework, said framework and said reflective means defining sidewalls and a top wall of the tunnel;

an opening substantially at an end of the tunnel for permitting movement of an item to be inspected into and out of the tunnel; and a light source within the tunnel for directing light on to said reflective means and thus on to the item to be inspected, said light source having a first source and a second source, the first source being generally directed toward the side wall and the second source being generally directed toward the top wall.

2. A light tunnel as set forth in claim 1, the framework including an outer structure and an inner assembly, the inner assembly being attached to an outer surface of the reflective means.

3. A light tunnel as set forth in claim 2, the outer structure comprising a plurality of arched members, spaced longitudinally along a length of the tunnel.

4. A light tunnel as set forth in claim 3, the inner assembly including a plurality of horizontally extending stringers carried by said arched members, said stringers extending the length of the tunnel, said stringers being attached to the outer surface of the reflective means.

5. A light tunnel as set forth in claim 4, there being substantially vertically extending braces positioned between the longitudinally extending stringers to add strength to the inner assembly.

6. A light tunnel as set forth in claim 1, there being closure means for the opening.

7. A light tunnel as set forth in claim 1, the tunnel having longitudinal and vertical dimensions sufficient to permit placement therein of an item to be inspected, the item being vehicular in nature.

8. A light tunnel as set forth in claim 1, the light from said first source and said second source being reflected by an inner surface of the side wall and the top wall onto a vehicle to be inspected when the vehicle is within the tunnel.

9. A light tunnel as set forth in claim 1 wherein the opening comprises an ingress opening and further comprising an egress opening at an opposite end of the tunnel from the ingress opening.

* * * * *